United States Patent [19]

Sawaki et al.

[11] 3,950,420

[45] Apr. 13, 1976

[54] CYCLOHEXANE DERIVATIVES

[75] Inventors: Mikio Sawaki; Isao Iwataki, both of Odawara; Yoshihiko Hirono, Hiratsuka; Hisao Ishikawa, Odawara, all of Japan

[73] Assignee: Nippon Soda Company, Ltd., Tokyo, Japan

[22] Filed: July 22, 1974

[21] Appl. No.: 490,349

[30] Foreign Application Priority Data
Aug. 15, 1973 Japan.............................. 48-91425
Mar. 7, 1974 Japan.............................. 49-25714

[52] U.S. Cl.................... 260/563 C; 71/88; 71/90; 71/97; 71/105; 71/114; 71/106; 260/468 J; 260/464; 260/347.7; 260/329 AM; 260/438.1; 260/439 R; 260/429 CY; 424/275; 424/278; 424/294; 424/295; 424/287; 424/304; 424/305

[51] Int. Cl.²........................................ C07C 87/36
[58] Field of Search ............................... 260/563 C

[56] References Cited
OTHER PUBLICATIONS
Bite et al., J. Org. Chem. U.S.S.R. 6, 2044–2045, (1970).

Primary Examiner—D. Horwitz
Attorney, Agent, or Firm—George B. Oujevolk

[57] ABSTRACT

Various substituted cyclohexane-1,3-diones are useful as herbicides.

An exemplary species is 2-[1-(allyloxyamino)propylidene]5,5-dimethylcyclohexane-1,3-dione.

11 Claims, 4 Drawing Figures

CYCLOHEXANE DERIVATIVES

DETAILED DESCRIPTION OF THE INVENTION:

Figure 1:
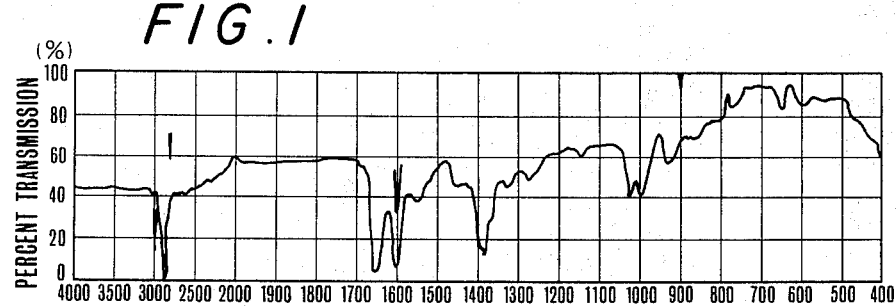

This invention relates to novel compounds of cyclohexane derivatives, to a process for the preparation of these compounds and their uses as selective herbicides.

In particularly this invention relates to new herbicidally active compositions and to method for killing undesired plants.

It has been found that outstanding herbicidal activity can be obtained by applying to the weed habitat, the compounds represented by the following formula:

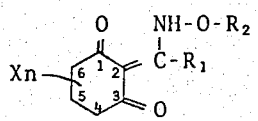

[I]

wherein
$R_1$ is selected from the group consisting of hydrogen, alkyl and phenyl,
$R_2$ is selected from the group consisting of alkyl, straight or branched chain lower alkenyl, lower alkynyl, lower alkoxyalkyl, lower alkyl-thiomethyl, lower alkoxycarbonyl-alkyl and benzyl,
X is a same or different substituent which is selected from the group consisting of alkyl, lower alkoxycarbonyl, halogen, cyano, phenyl, phenyl substituted with halogen or methoxy, styryl, furyl, thienyl, 5,5-pentamethylene and 4,5-tetramethylene,
n is 0 or an integer from 1 to 6;
or a hydrate or a metal salt of the compound defined herein above.

Preferred are those compounds represented by the following formula:

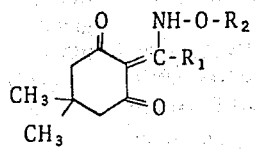 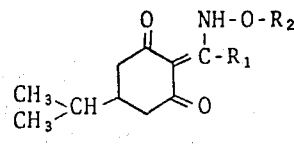

[II] [III]

wherein $R_1$ is ethyl or propyl group and $R_2$ is ethyl, propyl, allyl or propargyl group.

Particularly preferred because of their high order of herbicidal activity are:
  2-[1-(allyloxyamino)propylidene]-5,5-dimethylcyclohexane-1,3-dione
  2-[1-(allyloxyamino)butylidene]-5,5-dimethylcyclohexane-1,3-dione
  2-[1-(propargyloxyamino)butylidene]-5,5-dimethyl-cyclohexane-1,3-dione
  2-[1-(ethoxyamino)propylidene]-5-isopropylcyclohexane-1,3-dione
  2-[1-(allyloxyamino)propylidene]-5-isopropylcyclohexane-1,3-dione It is expected that the said compound represented by the above formula [I] has the following three chemical formulae because of tautomerism:

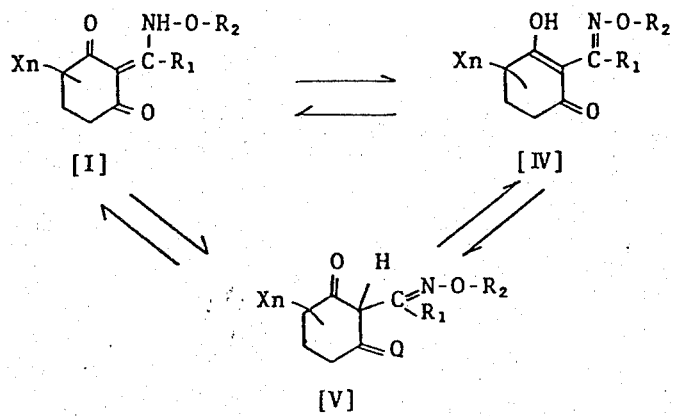

An explanation of the drawing

Figure 2:
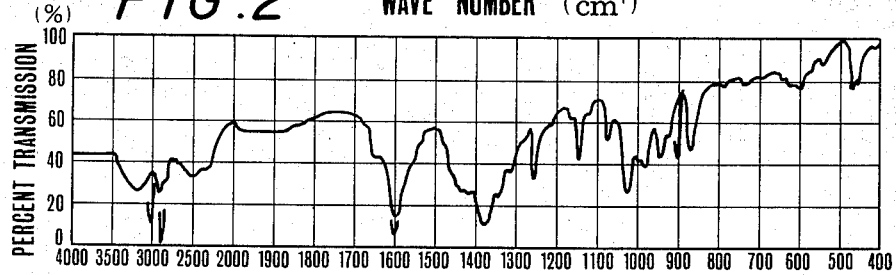
Figure 3:
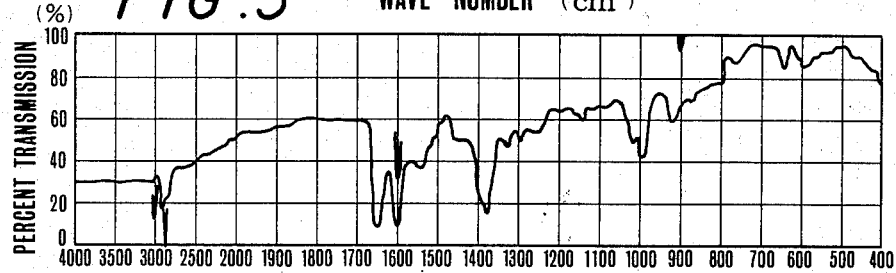
Figure 4:
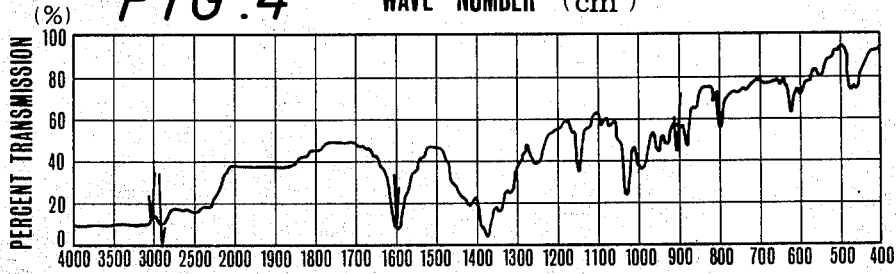

FIG. 1 is the infrared spectrum of 2-[1-(allyloxyamino)propylidene]-5,5-dimethyl-cyclohexane-1,3-dione FIG. 2 is the infrared spectrum of 2-[1(allyloxyamino)propylidene]-5,5-dimethyl-cyclohexane-1,3-dione hydrate FIG. 3 is the infrared spectrum of 2-[1-(allyloxyamino)butylidene]-5,5-dimethyl cyclohexane-1,3-dione FIG. 4 is the infrared spectrum of 2-[1-(allyloxyamino)butylidene]-5,5-dimethyl-cyclohexane-1,3-dione hydrate The compounds of this invention can be prepared in accordance with the following equation:

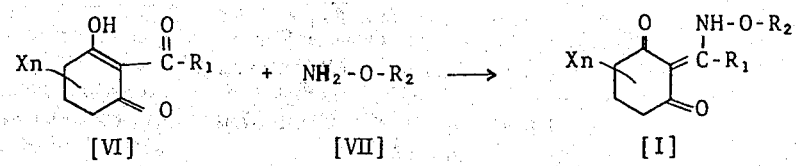

[VI] [VII] [I]

wherein $R_1$, $R_2$, X and n are as previously defined.

The above reaction can be conducted in an inert solvent.

As an inert solvent, acetone, ether, methylalcohol, ethylalcohol, isopropylalcohol, benzene, tetrahydrofuran, chloroform, acetonitrile, dichloroethane, dichloromethane, ethyl acetate, dioxane, toluene, xylene and dimethyl sulfoxide etc. are used.

Reaction temperature is from $-10°C$ to the boiling point of solvent employed, preferably from 10 to 60 and the reaction terminates between 0.5 and several hours.

After the reaction has terminated, the solvent, if necessary, is replaced and then, the reaction mixture is extracted with an alkaline solution and further, an alkaline layer is acidified with hydrochloric acid, whereby the crude product is isolated from the reaction mixture by extraction with solvent or by filtration.

In case of crystalline substance, the crude product can be purified by recrystallization and in oily substance the crude product can be purified by distillation or isolation by column chromatography.

A chemical formula for the resulting purified compound can be confirmatively identified by means of an elementary analysis, NMR spectrum and IR spectrum.

When above formula [VI] represents 5,5-dimethyl-2-acyl-3-hydroxy-2-cyclohexene-1-one, above starting compound can be prepared in accordance with the following equation:

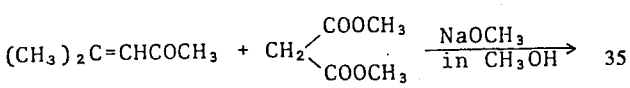

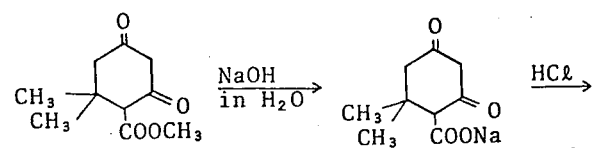

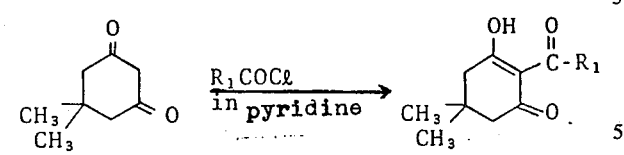

wherein $R_1$ is as previously defined.

It is also expected that the starting compound represented by the formula [VI] has the same three chemical formulas as the formula [I] because of tautomerism.

The sodium and potassium salts are prepared by treating a compound of formula [I] above with a sodium or potassium hydroxide in aqueous solution or an organic solvent such as acetone, methanol, ethanol, or dimethylformamide. The salts are isolated by filtration or by evaporation of the resulting solution.

The calcium, barium, manganese, copper, zinc, nickel, cobalt, iron and silver salts are prepared from the sodium salt by treatment with the appropriate inorganic metal salt, e.q. calcium chloride, barium chloride, copper sulfate, zinc chloride, nickel chloride, and cobalt nitrate.

The calcium salt is also prepared by treating a compound of formula [I] above with calcium hydroxide.

Some metal salt of the present invention produced with the above mentioned process may cause partially a chemical change or a decomposition at a high temperature, so that it does not show a clear melting point. Therefore, by applying infrared ray absorptive spectrum to the raw material and the reaction compound, a formation of the metal salt an be identified through a transference of absorption band and a change of absorption intensity. In other words, the raw material compound having the said general formula [I] indicates an absorption of carbonyl group at a wavelength $1605cm^{-1}$ and $1655cm^{-1}$, whereas the corresponding metal salt shows the absorption at a side of longer wavelength. Further, in some occasion, an anion such as OH may be simultaneously coordinated with a metal atom of some metal salt obtained above.

Some of the compounds of this invention may form a hydrates thereof as follows:

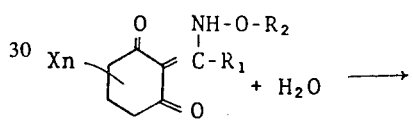

[I]

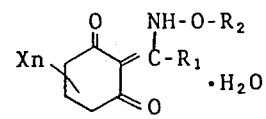

[VIII]

wherein $R_1$, $R_2$, X and n are as previously defined.

The hydrate of the compound of the invention also has superior herbicidal activity.

In order to facilitate a clear understanding of the invention, the following preferred specific embodiments are described as illustrative and not as limiting the invention.

Example 1

Preparation of 2-[1-(ethoxyamino)ethylidene]-5,5-dimethylcyclohexane-1,3-dione 1.8g (0.01 mol) of 2-acetyl-5,5-dimethyl-3-hydroxy-2-cyclohexene-1-one was dissolved in 10ml of ethanol and 0.6g (0.01 mol) of ethoxyamine was added to it and the resulting solution as stirred at a room temperature during 3 hours and then, the said ethanol was distilled off under a reduced pressure and a residual material was dissolved in chloroform.

The resulting chloroform solution was extracted two times with aqueous solution containing 5 weight percent of sodium hydroxide and an alkaline layer produced was acidified with hydrochloric acid and then an oily material was separated and extracted for two times with 10 ml of chloroform.

A chloroform layer produced was washed with water and it was dried and then, it was distilled off under a reduced pressure and thereby, the objective compound, as a colorless, oily material was obtained.

yield amount: 2.1g (93 weight percent of yield rate)
refractive index: $n_D^{21.5}$ 1.5094

Example 2

The following compounds (C) can be synthesized by the method of Example 1 substituting the appropriate substituted 2-acyl-3-hydroxy-2-cyclohexene-1-one (A) for 2-acetyl-5,5-dimethyl-3-hydroxy-2-cyclohexene-1-one and the appropriate O-substituted hydroxyamine (B) for ethoxyamine.

Compound No. 31

A. 5,5-Dimethyl-3-hydroxy-2-propyonyl-2-cyclohexene-1-one, 1.96g
B. Ethoxyamine, 0.67g
C. 2-[1-(ethoxyamino)propylidene]-5,5-dimethylcyclohexane-1,3-dione, yield amount: 2.3g (97 weight percent of yield rate)
refractive index: $n_D^{24}$ 1.5027

Compound No. 50

A. 5,5-Dimethyl-3-hydroxy-2-propyonyl-2-cyclohexene-1-one, 3.92g
B. Allyloxyamine, 1.6g
C. 2-[1-(allyloxyamino)propylidene]-5,5-dimethylcyclo-hexane-1,3-dione,
yield amount: 4.6g (92 weight percent of yield rate)
refractive index: $n_D^{24}$ 1.5119

Compound No. 75

A. 2-Butyryl-5,5-dimethyl-3-hydroxy-2-cyclohexene-1-one, 2.1g
B. Ethoxyamine, 0.67g
C. 2-[1-(Ethoxyamino)butylidene]-5,5-dimethylcyclohexane-1,3-dione,
yield amount: 2.1g (83 weight percent of yield rate)
refractive index: $n_D^{21}$ 1.4965

Compound No. 83

A. 2-Butyryl-5,5-dimethyl-3-hydroxy-2-cyclohexene-1-one, 2.1g
B. Allyloxyamine, 0.8g
C. 2-[1-(Allyloxyamino)butylidene]-5,5-dimethylcyclohexane-1,3-dione,
yield amount: 2.2g (83 weight percent of yield rate)
refractive index: $n_D^{21}$ 1.5089

Compound No. 96

A. 2-Butyryl-5,5-dimethyl-3-hydroxy-2-cyclohexene-1-one, 2.1g
B. Hexyloxyamine, 1.29g
C. 2-[1-(Hexyloxyamino)butylidene]-5,5-dimethylcyclohexane-1,3-dione,
yield amount: 2.5g (81 weight percent of yield rate)
refractive index: $n_D^{25}$ 1.4725

Example 3

2-[1-(allyloxyamino)ethylidene]-5,5-dimethylcyclohexane-1,3-dione 1.8g (0.01 mol) of 2-acetyl-5,5-dimethyl-3-hydroxy-2-cyclohexene-1-one was dissolved in 10 ml of ethanol and then, 0.73g (0.01 mol) of allyloxyamine was added in it and the resulting solution was agitated at 50°C during 1 hour and then, the said ethanol was distilled off under a reduced pressure and a residual material was dissolved in chloroform.

The resulting chloroform solution was extracted for two times with 7 ml of an aqueous solution containing 10 weight percent of caustic soda. An alkaline layer produced thereto was acidified with hydrochloric acid and a separated crystal was filtered and washed with water and then, it was dried. Then, the said crystal was recrystallized from n-hexane and thereby, the objective compound was obtained as a colorless crystal.

A yield amount: 2.2g (93 weight percent of yield rate)
A melting point: 30.5 to 31.5°C

Example 4

Cobalt salt of 2-[1-(allyloxyamino)propylidene]-5,5-dimethylcyclohexane-1,3-dione Two gram of 2-[1-(allyloxyamino)propylidene]-5,5-dimethyl-cyclohexane-1,3-dione were dissolved in 10ml of acetone, and to which 20ml of water containing 0.32g of sodium hydroxide were added. After stirring 10 minutes, 5ml of water containing 1.16g of cobalt nitrate [CO(NO_3)_2·6H_2O] were added dropwise to the mixture. After stirring well, the precipitate was filtrated, washed with water and ether and dried. Gray crystal having a decomposition point of 153°–154°C was obtained.

yield amount: 2.2g (98 weight percent of yield rate)

Example 5

The following compounds (C) can be synthesized by the method of Example 4 substituting the appropriate substituted cyclohexane-1,3-dione (A) for 2-[1-(allyloxyamino)propylidene]-5,5-dimethylcyclohexane-1,3-dione, the appropriate inorganic metal salt (B) for cobalt nitrate, and the appropriate amount of sodium hydroxide (D).

Compound No. 141

A. 2-[1-(allyloxyamino)butylidene]-5,5-dimethylcyclohexane-1,3-dione (2.1g)
B. Nickel chloride $NiCl_2 \cdot 6H_2O$ (0.95g)
C. Nickel salt of 2-[1-(allyloxyamino)butylidene]-5,5-dimethylcyclohexane-1,3-dione (2.2g), 94 weight percent of yield rate, decomposition point: over 250°C
D. Sodium hydroxide (0.32g)

Compound No. 150

A. 2-[-1-(benzyloxyamino)butylidene]-5,5-dimethyl-cyclohexane-1,3-dione (3.1g)
B. Copper sulfate $CuSO_4 \cdot 5H_2O$ (1.25g)
C. Copper salt of 2-[1-(benzyloxyamino)butylidene]-5,5-dimethylcyclohexane-1,3-dione (3.2g), 93 weight percent of yield rate, decomposition point: 126°–127°C
D. Sodium hydroxide (0.4g)

Compound No. 112

A. 2-[1-(allyloxyamino)ethylidene]-5-phenylcyclohexane-1,3-dione (2.8g)
B. Copper sulfate $CuSO_4 \cdot 5H_2O$ (0.125g)
C. Copper salt of 2-[1-(allyloxyamino)ethylidene]-5-phenyl-cyclohexane-1,3-dione (3g), 95 weight percent of yield rate, decomposition point: 188°–189°C D. Sodium hydroxide (0.4g)

Example 6

Sodium salt of 2-[1-(allyloxyamino)butylidene]-5,5-dimethylcyclohexane-1,3-dione 2.6g of 2-[1-(allyloxyamino)butylidene]-5,5-dimethyl-cyclohexane-1,3-dione was dissolved in 20ml of acetone. 0.4g of sodium hydroxide dissolved in 5ml of water was added to the solution. The solvent was evaporated at reduced pressure after stirring 10 minutes. While crystal having a melting point of 80° to 82°C was obtained by crystallizing the glass-state substance from the mixture of ethanol and benzene.

Yield amount: 2.6g (91 weight percent of yield rate)

Example 7.

Calcium salt of 2-[1-(allyloxyamino)propylidene]-5,5-dimethylcyclohexane-1,3-dione 2.5g of 2-[1-(allyloxyamino)propylidene]-5,5-dimethyl-cyclohexane-1,3-dione was dissolved in 20ml of ethanol. 0.37g of calcium hydroxide dissolved in 20ml of water was added little by little to the solution under stirring. After stirring 1 hr. the insoluble substance was filtrated. The filtrate was evaporated at reduced pressure and precipitated white crystal was washed and dried.

Yield amount: 2.7g (100 weight percent of yield rate)

Decomposition point: 107° – 108°C

Example 8.

2-[1-(allyloxyamino)butylidene]-5,5-dimethylcyclohexane-1,3-dione hydrate 2.65g of 2-[1-(allyloxyamino)butylidene]-5,5-dimethylcyclohexane-1,3-dione was added to 10ml of water and the mixture was vigorously stirred. After several minutes, the precipitate was filtered, washed with water and dried. White crystal having a melting point of 46°–47°C was obtained.

Yield amount: 2.8g (100 weight percent of yield rate)

Example 9

The following hydrate compounds (B) can be obtained by the method of Example 8 substituting the appropriate substituted cyclohexane-1,3-dione (A) for 2-[1-(allyloxyamino)-butylidene]-5,5-dimethylcyclohexane-1,3-dione.

Compound No. 154

A. 2-[1-(allyloxyamino)propylidene]-5-methylcyclohexane-1,3-dione (2.37g)

B. 2-[1-(allyloxyamino)propylidene]-5-methylcyclohexane-1,3-dione hydrate (2.5g)

yield rate: 100 weight percent, m.p. : 46° – 48°C

Compound No. 156

A. 2-[1-(ethoxyamino)propylidene]-5-phenylcyclohexane-1,3-dione (2.87g)

B. 2-[1-(ethoxyamino)propylidene]-5-phenylcyclohexane-1,3-dione hydrate (3.0g)

yield rate: 100 weight percent, m.p.: 67° – 68°C

In addition to the above mentioned compounds described in the preceding example, some typical compounds of the present invention are listed in Table 1.

Table 1

| Compd. No. | Chemical Name | Physical Constant |
| --- | --- | --- |
| 1 | 2-[1-(allyloxyamino)methylidene]-5,5-dimethylcyclohexane-1,3-dione | m.p. 55–60°C |
| 2 | 2-[1-(ethoxyamino)ethylidene]-cyclohexane-1,3-dione | m.p. 48–50°C |
| 3 | 2-[1-(ethoxyamino)ethylidene]-4-cyano-5,5-dimethylcyclohexane-1,3-dione | $n_D^{23.5}1.5280$ |
| 4 | 2-[1-(ethoxyamino)ethylidene]-4-isopropylcyclohexane-1,3-dione | $n_D^{24}1.5115$ |
| 5 | 2-[1-(ethoxyamino)ethylidene]-4-ethoxycarbonyl-4-ethylcyclohexane-1,3-dione | $n_D^{22.5}1.5047$ |
| 6 | 2-[1-(ethoxyamino)ethylidene]-4-bromo-5,5-dimethylcyclohexane-1,3-dione | $n_D^{23}1.5405$ |
| 7 | 2-[1-(ethoxyamino)ethylidene]-4-ethoxycarbonyl-5,5-dimethylcyclohexane-1,3-dione | $n_D^{21}1.5050$ |
| 8 | 2-[1-(ethoxyamino)ethylidene]-5-ethylcyclohexane-1,3-dione | $n_D^{24}1.5132$ |
| 9 | 2-[1-(ethoxyamino)ethylidene]-4-methoxycarbonyl-5,5-dimethylcyclohexane-1,3-dione | $n_D^{25}1.5065$ |
| 10 | 2-[1-(ethoxyamino)ethylidene]-5,5-dimethylcyclohexane-1,3-dione | $n_D^{21.5}1.5094$ |
| 11 | 2-[1-(ethoxyamino)ethylidene]-5-phenylcyclohexane-1,3-dione | m.p. 56–57°C |
| 12 | 2-[1-(allyloxyamino)ethylidene]-cyclohexane-1,3-dione | m.p. 55–57°C |
| 13 | 2-[1-(allyloxyamino)ethylidene]-4-bromo-5,5-dimethylcyclohexane-1,3-dione | $n_D^{31}1.5468$ |
| 14 | 2-[1-(allyloxyamino)ethylidene]-4-cyano-5,5-dimethylcyclohexane-1,3-dione | m.p. 78–80°C |
| 15 | 2-[1-(allyloxyamino)ethylidene]-4-ethoxycarbonyl-5,5-dimethylcyclohexane-1,3-dione | $n_D^{21}1.5128$ |
| 16 | 2-[1-(allyloxyamino)ethylidene]-4-methoxycarbonyl-5,5-dimethylcyclohexane-1,3-dione | $n_D^{26}1.5095$ |
| 17 | 2-[1-(allyloxyamino)ethylidene]-5- | $n_D^{26}1.5203$ |

Table 1-continued

| Compd. No. | Chemical Name | Physical Constant |
|---|---|---|
| | ethylcyclohexane-1,3-dione | |
| 18 | 2-[1-(allyloxyamino(ethylidene]-5,5-dimethylcyclohexane-1,3-dione | m.p. 30.5–31.5°C |
| 19 | 2-[1-(allyloxyamino)ethylidene]-5-phenylcyclohexane-1,3-dione | m.p. 34–35°C |
| 20 | 2-[1-(propoxyamino)ethylidene]-5,5-dimethylcyclohexane-1,3-dione | $n_D^{18.5}1.5088$ |
| 21 | 2-[1-(ethoxyamino)propylidene]-cyclohexane-1,3-dione | $n_D^{24.5}1.5188$ |
| 22 | 2-[1-(ethoxyamino)propylidene]-5-(4-methylphenyl)cyclohexane-1,3-dione | m.p. 65–66°C |
| 23 | 2-[1-(ethoxyamino)propylidene]-5-(3-chlorophenyl)cyclohexane-1,3-dione | m.p. 44–45°C |
| 24 | 2-[1-(ethoxyamino)propylidene]-5-(4-methoxyphenyl)cyclohexane-1,3-dione | m.p. 59–60°C |
| 25 | 2-[1-(ethoxyamino)propylidene]-5-(4-chlorophenyl)cyclohexane-1,3-dione | m.p. 92–93°C |
| 26 | 2-[1-(ethoxyamino)propylidene]-5-phenylcyclohexane-1,3-dione | m.p. 67–68°C |
| 27 | 2-[1-(ethoxyamino)propylidene]-5-styrylcyclohexane-1,3-dione | m.p. 92–96°C |
| 28 | 2-[1-(ethoxyamino)propylidene]-5-(2-furyl)cyclohexane-1,3-dione | m.p. 50–52°C |
| 29 | 2-[1-(ethoxyamino)propylidene]-5-(2-thienyl)cyclohexane-1,3-dione | m.p. 68–69°C |
| 30 | 2-[1-(ethoxyamino)propylidene]-5-methylcyclohexane-1,3-dione | $n_D^{20}1.5045$ |
| 31 | 2-[1-(ethoxyamino)propylidene]-5,5-dimethylcyclohexane-1,3-dione | $n_D^{24}1.5027$ |
| 32 | 2-[1-(ethoxyamino)propylidene]-5-isopropylcyclohexane-1,3-dione | $n_D^{18}1.5111$ |
| 33 | 2-[1-(ethoxyamino)propylidene]-5-hexylcyclohexane-1,3-dione | $n_D^{18.5}1.5019$ |
| 34 | 2-[1-(ethoxyamino)propylidene]-4-methyl-5,5-dimethylcyclohexane-1,3-dione | $n_D^{21}1.5081$ |
| 35 | 2-[1-(ethoxyamino)propylidene]-4,4-dimethylcyclohexane-1,3-dione | $n_D^{18}1.4946$ |
| 36 | 2-[1-(ethoxyamino)propylidene]-4-cyano-5,5-dimethylcyclohexane-1,3-dione | m.p. 47–48°C |
| 37 | 2-[1-(ethoxyamino)propylidene]-4-methoxycarbonyl-5,5-dimethylcyclohexane-1,3-dione | $n_D^{24}1.5070$ |
| 38 | 2-[1-(ethoxyamino)propylidene]-4-ethoxycarbonyl-5,5-dimethylcyclohexane-1,3-dione | $n_D^{18}1.5040$ |
| 39 | 2-[1-(ethoxyamino)propylidene]-4-n-propylcyclohexane-1,3-dione | $n_D^{25}1.5078$ |
| 40 | 2-[1-(ethoxyamino)propylidene]-4-iso-butylcyclohexane-1,3-dione | $n_D^{21}1.5055$ |
| 41 | 2-[1-(methoxymethoxyamino)propylidene]-5,5-dimethylcyclohexane-1,3-dione | $n_D^{27}1.5017$ |
| 42 | 2-[1-(buthoxymethoxyamino)propylidene]-5,5-dimethylcyclohexane-1,3-dione | $n_D^{27}1.4927$ |
| 43 | 2-[1-(methylthiomethoxyamino)propylidene]-5,5-dimethylcyclohexane-1,3-dione | $n_D^{27}1.5582$ |
| 44 | 2-[1-(methylthiomethoxyamino)propylidene]-5-isopropylcyclohexane-1,3-dione | $n_D^{27}1.5328$ |
| 45 | 2-[1-(methoxyethoxyamino)propylidene]-5,5-dimethylcyclohexane-1,3-dione | $n_D^{20}1.5100$ |
| 46 | 2-[1-(ethoxycarbonylmethoxyamino)propylidene]-4,4-dimethylcyclohexane-1,3-dione | $n_D^{20}1.5019$ |
| 47 | 2-[1-(propoxyamino)propylidene]-5,5-dimethylcyclohexane-1,3-dione | $n_D^{26}1.4994$ |
| 48 | 2-[1-(allyloxyamino)propylidene]-cyclohexane-1,3-dione | $n_D^{25}1.5265$ |
| 49 | 2-[1-(allyloxyamino)propylidene]-5-methylcyclohexane-1,3-dione | $n_D^{20.5}1.5200$ |
| 50 | 2-[1-(allyloxyamino)propylidene]-5,5-dimethylcyclohexane-1,3-dione | $n_D^{24}1.5119$ |
| 51 | 2-[1-(allyloxyamino)propylidene]-5-isopropylcyclohexane-1,3-dione | $n_D^{20.5}1.5140$ |
| 52 | 2-[1-(allyloxyamino)propylidene]-5-hexylcyclohexane-1,3-dione | $n_D^{18.5}1.5082$ |
| 53 | 2-[1-(allyloxyamino)propylidene]-5-(2-furyl)cyclohexane-1,3-dione | $n_D^{22}1.5452$ |
| 54 | 2-[1-(allyloxyamino)propylidene]-5-phenylcyclohexane-1,3-dione | m.p. 48–50°C |
| 55 | 2-[1-(allyloxyamino)propylidene]-5-styrylcyclohexane-1,3-dione | $n_D^{21}1.5851$ |
| 56 | 2-[1-(allyloxyamino)propylidene]-4-bromo-6,6-dimethylcyclohexane-1,3-dione | $n_D^{27}1.5338$ |
| 57 | 2-[1-(allyloxyamino)propylidene]-4-bromo-5,5-dimethylcyclohexane-1,3-dione | $n_D^{26}1.5365$ |
| | 2-[1-(allyloxyamino)propylidene]-4- | |

Table 1-continued

| Compd. No. | Chemical Name | Physical Constant |
|---|---|---|
| 58 | cyano-5,5-dimethylcyclohexane-1,3-dione | m.p. 62–63°C |
| 59 | 2-[1-(allyloxyamino)propylidene]-4-methoxycarbonyl-5,5-dimethylcyclohexane-1,3-dione | $n_D^{24.5}$ 1.5088 |
| 60 | 2-[1-(allyloxyamino)propylidene]-4-ethoxycarbonyl-5-methylcyclohexane-1,3-dione | $n_D^{20}$ 1.5146 |
| 61 | 2-[1-(allyloxyamino)propylidene]-4-ethoxycarbonyl-5,5-dimethylcyclohexane-1,3-dione | $n_D^{18}$ 1.5079 |
| 62 | 2-[1-(allyloxyamino)propylidene]-4-ethoxycarbonyl-4-ethycyclohexane-1,3-dione | $n_D^{22}$ 1.5078 |
| 63 | 2-[1-(allyloxyamino)propylidene]-4-methyl-5,5-dimethylcyclohexane-1,3-dione | $n_D^{21}$ 1.5138 |
| 64 | 2-[1-(allyloxyamino)propylidene]-4,4-dimethylcyclohexane-1,3-dione | $n_D^{18}$ 1.5138 |
| 65 | 2-[1-(allyloxyamino)propylidene]-4-isopropylcyclohexane-1,3-dione | $n_D^{20}$ 1.5152 |
| 66 | 2-[1-(allyloxyamino)propylidene]-4-n-propylcyclohexane-1,3-dione | $n_D^{25}$ 1.5103 |
| 67 | 2-[1-(allyloxyamino)propylidene]-4-n-butylcyclohexane-1,3-dione | $n_D^{21.5}$ 1.5134 |
| 68 | 2-[1-(allyloxyamino)propylidene]-4-n-pentylcyclohexane-1,3-dione | $n_D^{25}$ 1.5091 |
| 69 | 2-[1-(propargyloxyamino)propylidene]-5,5-dimethylcyclohexane-1,3-dione | $n_D^{18.5}$ 1.5218 |
| 70 | 2-[1-(methallyloxyamino)propylidene]-5,5-dimethylcyclohexane-1,3-dione | $n_D^{23}$ 1.5107 |
| 71 | 2-[1-(n-butoxyamino)propylidene]-5,5-dimethylcyclohexane-1,3-dione | $n_D^{18.5}$ 1.5027 |
| 72 | 2-[1-(isobutoxyamino)propylidene]-5,5-dimethylcyclohexane-1,3-dione | $n_D^{23}$ 1.4976 |
| 73 | 2-[1-(benzyloxyamino)propylidene]-5,5-dimethylcyclohexane-1,3-dione | m.p. 58–59°C |
| 74 | 2-[1-(methoxyamino)butylidene]-5,5-dimethylcyclohexane-1,3-dione | $n_D^{23}$ 1.4940 |
| 75 | 2-[1-(ethoxyamino)butylidene]-5,5-dimethylcyclohexane-1,3-dione | $n_D^{21}$ 1.4965 |
| 76 | 2-[1-(ethoxyamino)butylidene]-5-isopropylcyclohexane-1,3-dione | $n_D^{18}$ 1.5068 |
| 77 | 2-[1-(ethoxyamino)butylidene]-5-hexylcyclohexane-1,3-dione | $n_D^{18.5}$ 1.5005 |
| 78 | 2-[1-(ethoxyamino)butylidene]-4-cyano-5,5-dimethylcyclohexane-1,3-dione | m.p. 83–87°C |
| 79 | 2-[1-(ethoxyamino)butylidene]-4-methoxycarbonyl-5,5-dimethylcyclohexane-1,3-dione | $n_D^{24.5}$ 1.5007 |
| 80 | 2-[1-(ethoxyamino)butylidene]-4-ethoxycarbonyl-5,5-dimethylcyclohexane-1,3-dione | $n_D^{21.5}$ 1.4990 |
| 81 | 2-[1-(ethoxyamino)butylidene]-4,4-dimethylcyclohexane-1,3-dione | $n_D^{20}$ 1.5050 |
| 82 | 2-[1-(isopropoxyamino)butylidene]-5,5-dimethylcyclohexane-1,3-dione | $n_D^{31}$ 1.4939 |
| 83 | 2-[1-(allyloxyamino)butylidene]-5,5-dimethylcyclohexane-1,3-dione | $n_D^{21}$ 1.5089 |
| 84 | 2-[1-(allyloxyamino)butylidene]-5-isopropylcyclohexane-1,3-dione | $n_D^{18}$ 1.5135 |
| 85 | 2-[1-(allyloxyamino)butylidene]-5-hexylcyclohexane-1,3-dione | $n_D^{18.5}$ 1.5051 |
| 86 | 2-[1-(allyloxyamino)butylidene]-5-(4-methoxyphenyl)cyclohexane-1,3-dione | m.p. 52–53°C |
| 87 | 2-[1-(allyloxyamino)butylidene]-5-(3-chlorophenyl)cyclohexane-1,3-dione | $n_D^{25.5}$ 1.5657 |
| 88 | 2-[1-(allyloxyamino)butylidene]-5-(4-chlorophenyl)cyclohexane-1,3-dione | m.p. 36–37°C |
| 89 | 2-[1-(allyloxyamino)butylidene]-4-cyano-5,5-dimethylcyclohexane-1,3-dione | m.p. 105–108°C |
| 90 | 2-[1-(allyloxyamino)butylidene]-4-methoxycarbonyl-5,5-dimethylcyclohexane-1,3-dione | $n_D^{24.5}$ 1.5063 |
| 91 | 2-[1-(allyloxyamino)butylidene]-4-ethoxycarbonyl-5,5-dimethylcyclohexane-1,3-dione | $n_D^{21}$ 1.5066 |
| 92 | 2-[1-(allyloxyamino)butylidene]-4-ethoxycarbonyl-4-ethylcyclohexane-1,3-dione | $n_D^{22.5}$ 1.5078 |
| 93 | 2-[1-(allyloxyamino)butylidene]-4,4-dimethylcyclohexane-1,3-dione | $n_D^{18}$ 1.4753 |
| 94 | 2-[1-(allyloxyamino)butylidene]-4-isopropylcyclohexane-1,3-dione | $n_D^{23.5}$ 1.5058 |
| 95 | 2-[1-(propargyloxyamino)butylidene]-5,5-dimethylcyclohexane-1,3-dione | $n_D^{31}$ 1.5132 |
| 96 | 2-[1-(hexyloxyamino)butylidene]-5,5-dimethylcyclohexane-1,3-dione | $n_D^{25}$ 1.4725 |
| 97 | 2-[1-(ethoxyamino)isobutylidene]-5,5-dimethylcyclohexane-1,3-dione | $n_D^{23}$ 1.5013 |

Table 1-continued

| Compd. No. | Chemical Name | Physical Constant |
|---|---|---|
| 98 | 2-[1-(ethoxyamino)hexylidene]-5,5-dimethylcyclohexane-1,3-dione | $n_D^{31}$ 1.4881 |
| 99 | 2-[1-(allyloxyamino)hexylidene]-5,5-dimethylcyclohexane-1,3-dione | $n_D^{31}$ 1.5040 |
| 100 | 2-[1-(ethoxyamino)benzylidene]-5,5-dimethylcyclohexane-1,3-dione | m.p. 150–151°C |
| 101 | 2-[1-(allyloxyamino)benzylidene]-5,5-dimethylcyclohexane-1,3-dione | m.p. 169–170°C |
| 102 | 2-[1-(ethoxyamino)propylidene]-5,5-pentamethylenecyclohexane-1,3-dione | $n_D^{21}$ 1.5272 |
| 103 | 2-[1-(allyloxyamino)propylidene]-5,5-pentamethylenecyclohexane-1,3-dione | $n_D^{21}$ 1.5336 |
| 104 | 2-[1-(ethoxyamino)propylidene]-4,5-tetramethylenecyclohexane-1,3-dione | $n_D^{21}$ 1.5282 |
| 105 | 2-[1-(allyloxyamino)propylidene]-4,5-tetramethylenecyclohexane-1,3-dione | $n_D^{21}$ 1.5347 |
| 106 | Manganese salt of 2-[1-(ethoxyamino)-ethylidene]-5,5-dimethylcyclohexane-1,3-dione | m.p. 225–226°C(d.) |
| 107 | Potassium Salt of 2-[1-(ethoxyamino)-ethylidene]-5,5-dimethylcyclohexane-1,3-dione | m.p. 110–112°C(d.) |
| 108 | Copper salt of 2-[1-(ethoxyamino)-ethylidene]-5,5-dimethylcyclohexane-1,3-dione | m.p. 156–157°C(d.) |
| 109 | Copper salt of 2-[1-(ethoxyamino)-ethylidene]-4-cyano-5,5-dimethylcyclohexane-1,3-dione | m.p. 161–164°C(d.) |
| 110 | Sodium salt of 2-[1-(ethoxyamono)-ethylidene]-4-methoxycarbonyl-5,5-dimethylcyclohexane-1,3-dione | m.p. 110–120°C(d.) |
| 111 | Copper salt of 2-[1-(allyloxyamino)-ethylidene]-5-ethylcyclohexane-1,3-dione | m.p. 164–165°C(d.) |
| 112 | Copper salt of 2-[1-(allyloxyamino)-ethylidene]-5-phenylcyclohexane-1,3-dione | m.p. 188–189°C(d.) |
| 113 | Copper salt of 2-[1-(allyloxyamino)ethylidene]-4-cyano-5,5-dimethylcyclohexane-1,3-dione | m.p. 154–158°C(d.) |
| 114 | Sodium salt of 2-[1-(allyloxyamino)-ethylidene]-4-methoxycarbonyl-5,5-dimethylcyclohexane-1,3-dione | m.p. 193–194°C(d.) |
| 115 | Sodium salt of 2-[1-(allyloxyamino)-ethylidene]-4-ethoxycarbonyl-5,5-dimethylcyclohexane-1,3-dione | m.p. 110–120°C(d.) |
| 116 | Copper salt of 2-[1-(methylthio-methoxyamino)propylidene]-5,5-dimethylcyclohexane-1,3-dione | m.p. 110°C(d.) |
| 117 | Copper salt of 2-[1-(ethoxyamino)-propylidene]-5-(1-furyl)cyclohexane-1,3-dione | m.p. 197–198°C(d.) |
| 118 | Copper salt of 2-[1-(ethoxyamino)-propylidene]-5-(2-thienyl)cyclohexane-1,3-dione | m.p. 184–185°C(d.) |
| 119 | Copper salt of 2-[1-(ethoxyamino)-propylidene]-5-(4-chlorophenyl)-cyclohexane-1,3-dione | m.p. 186–188°C(d.) |
| 120 | Copper salt of 2-[1-(ethoxyamino)-propylidene]-5-(3-chlorophenyl)-cyclohexane-1,3-dione | m.p. 184–185°C(d.) |
| 121 | Copper salt of 2-[1-(ethoxyamino)-propylidene]-5-(4-methylphenyl)-cyclohexane-1,3-dione | m.p. 183–184°C(d.) |
| 122 | Copper salt of 2-[1-(ethoxyamino)-propylidene]-4-cyano-5,5-dimethyl-cyclohexane-1,3-dione | m.p. 81–83°C(d.) |
| 123 | Sodium salt of 2-[1-(ethoxyamino)-propylidene]-4-ethoxycarbonyl-5,5-dimethylcyclohexane-1,3-dione | m.p. 188–190°C(d.) |
| 124 | Copper salt of 2-[1-(allyloxyamino)-propylidene]-cyclohexane-1,3-dione | m.p. 146–147°C(d.) |
| 125 | Copper salt of 2-[1-(allyloxyamino)-propylidene]-5-methylcyclohexane-1,3-dione | m.p. 129–130°C(d.) |
| 126 | Nickel salt of 2-[1-(allyloxyamino)-propylidene]-5,5-dimethylcyclohexane-1,3-dione | m.p. 169–170°C(d.) |
| 127 | Calcium salt of 2-[1-(allyloxyamino)-propylidene]-5,5-dimethylcyclohexane-1,3-dione | m.p. 107–108°C(d.) |
| 128 | Cobalt salt of 2-[1-(allyloxyamino)-propylidene]-5,5-dimethylcyclohexane-1,3-dione | m.p. 151–152°C(d.) |
| 129 | Copper salt of 2-[1-(allyloxyamino)-propylidene]-5-isopropylcyclohexane-1,3-dione | m.p. 145–146°C(d.) |
| 130 | Copper salt of 2-[1-(allyloxyamino)-propylidene]-4-cyano-5,5-dimethyl-cyclohexane-1,3-dione | m.p. 78–80°C(d.) |
| | Sodium salt of 2-[1-(allyloxyamino)- | |

Table 1-continued

| Compd. No. | Chemical Name | Physical Constant |
|---|---|---|
| 131 | propylidene]-4-methoxycarbonyl-5,5-dimethylcyclohexane-1,3-dione | m.p. 175–178°C(d.) |
| 132 | Sodium salt of 2-[1-(allyloxyamino)-propylidene]-4-ethoxycarbonyl-5,5-dimethylcyclohexane-1,3-dione | m.p. 110–120°C(d.) |
| 133 | Calcium salt of 2-[1-(allyloxyamino)-propylidene]-4-propylcyclohexane-1,3-dione | m.p. 150–152°C(d.) |
| 134 | Copper salt of 2-[1-(propargyloxyamino)propylidene]-5,5-dimethylcyclohexane-1,3-dione | m.p. 126–127°C(d.) |
| 135 | Barium salt of 2-[1-(propoxyamino)-propylidene]-5,5-dimethylcyclohexane-1,3-dione | m.p. 75–78°C(d.) |
| 136 | Calcium salt of 2-[1-(isobutoxyamino)-propylidene]-5,5-dimethylcyclohexane-1,3-dione | m.p. 195–200° C(d.) |
| 137 | Copper salt of 2-[1-(butoxyamino)-propylidene]-5,5-dimethylcyclohexane-1,3-dione | m.p. 123–125°C(d.) |
| 138 | Calcium salt of 2-[1-(ethoxyamino)-butylidene]-5,5-dimethylcyclohexane-1,3-dione | m.p. 180°C(d.) |
| 139 | Copper salt of 2-[1-(ethoxyamino)-butylidene]-4-cyano-5,5-dimethyl-cyclohexane-1,3-dione | m.p. 98–101°C(d.) |
| 140 | Sodium salt of 2-[1-(ethoxyamino)-butylidene]-4-methoxycarbonyl-5,5-dimethylcyclohexane-1,3-dione | m.p. 183–185°C(d.) |
| 141 | Nickel salt of 2-[1-(allyloxyamino)-butylidene]-5,5-dimethylcyclohexane-1,3-dione | >m.p. 250°C(d.) |
| 142 | Cobalt salt of 2-[1-(allyloxyamino)-butylidene]-5,5-dimethylcyclohexane-1,3-dione | m.p. 153–154°C(d.) |
| 143 | Sodium salt of 2-[1-(allyloxyamino)-butylidene]-5,5-dimethylcyclohexane-1,3-dione | m.p. 80–82°C |
| 144 | Copper salt of 2-[1-(allyloxyamino)-butylidene]-5-isopropylcyclohexane-1,3-dione | m.p. 145–146°C(d.) |
| 145 | Copper salt of 2-[1-(allyloxyamino)-butylidene]-5-hexcylcyclohexane-1,3-dione | m.p. 105–106°C(d.) |
| 146 | Copper salt of 2-[1-(allyloxyamino)-butylidene]-5-(4-methoxyphenyl)cyclohexane-1,3-dione | m.p. 182–183°C(d.) |
| 147 | Copper salt of 2-[1-(allyloxyamino)-butylidene]-4-cyano-5,5-dimethyl-cyclohexane-1,3-dione | m.p. 92–95°C(d.) |
| 148 | Sodium salt of 2-[1-(allyloxyamino)-butylidene]-4-methoxycarbonyl-5,5-dimethylcyclohexane-1,3-dione | m.p. 192°C(d.) |
| 149 | Sodium salt of 2-[1-(allyloxyamino)-butylidene]-4-ethoxycarbonyl-5,5-dimethylcyclohexane-1,3-dione | m.p. 110–120°C(d.) |
| 150 | Copper salt of 2-[1-(benzyloxyamino)-butylidene]-5,5-dimethylcyclohexane-1,3-dione | m.p. 126–127°C(d.) |
| 151 | Copper salt of 2-[1-(allyloxyamino)-propylidene]-4,5-tetramethylenecyclohexane-1,3-dione | m.p. 178–179°C(d.) |
| 152 | 2-[1-(allyloxyamino)butylidene]-5,5-dimethylcyclohexane-1,3-dione hydrate | m.p. 47–49°C |
| 153 | 2-[1-(allyloxyamino)propylidene]-5,5-dimethylcyclohexane-1,3-dione hydrate | m.p. 52–54°C |
| 154 | 2-[1-(allyloxyamino)propylidene]-5-methylcyclohexane-1,3-dione hydrate | m.p. 46–48°C |
| 155 | 2-[1-(allyloxyamino)propylidene]-5-phenylcyclohexane-1,3-dione hydrate | m.p. 48–50°C |
| 156 | 2-[1-(ethoxyamino)propylidene]-5-phenylcyclohexane-1,3-dione hydrate | m.p. 67–68°C |
| 157 | 2-[1-(allyloxyamino)propylidene]-5,5-diethylcyclohexane-1,3-dione | |

*m.p.: melting point
$n_D$ : refractive index
d. : decomposition

Hereinafter, the compounds of this invention are represented by Compound No. in Table 1.

As mentioned previously, it has been found that the compounds of the invention possess superior herbicidal activity. The paragraphs which follow described in more detail the utility of this invention.

The compounds of the invention are particularly effective in the control of grass weeds such as annual bluegrass (*Poa annua*), water foxtail (*Alopecurus aequalis*), large crabgrass (*Digitaria adscendens*), green foxtail (*Panicum viride L*), wild oat (*Avena fatua* L) etc. and they hardly injure broad leaf crops such as adzuki bean (*Phaseolus angularis*) and soy bean (*Glycine max*) and sugar beets which easily suffer phytotoxicity. Namely, the compounds of the invention are the selective herbicide.

It is already known that 4-hydroxy-6-methyl-α-pyrone derivatives has herbicidal properties as shown in Japanese patent publication No. 16916/1971.

But in order to destroy completely the said grass weeds, a large amount of the above herbicidal chemical is required and this is one drawback for above mentioned herbicidal compound.

In the other words, according to the descriptions of above mentioned prior art and the results of the later additional experiments by the inventors, a chemical amount containing 500g of effective ingredient, in proportion to 10 hectare ("hectare" is 100 square meters) of area is able to give an expected effect in the case of employing it practically, but another chemical amount containing 250g of effective ingredient, in proportion to 10 hectare of area is not able to wither grass weeds to death, in the other words, it cannot give a perfect herbicidal effect.

But, in the event of employing the compound of the present invention as a herbicide, a chemical amount containing 250g of effective component, as a matter of course, further a chemical amount containing 125g of less of effective ingredient, in proportion to 10 hectare of area, in compliance with the same treating method of conventional herbicide indicates a strong herbicidal effect and thereby a perfect prevention and extermination of weeds can be expected.

In case of foliar treatment using the compounds of the present invention, even the same amount of chemical which makes barnyard grass of grass weeds completely kill gives no damages to broadleaf plants such as radish, soy bean (*Glycine max*), garden pea (*Pisum sativum*), spinach (*Spinacia oleracea*) sugar beets and carrot at all, and in case of soil treatment before germination, even the same amount of chemicals which prevents large crab-grass (*Digitaria adscendens*) germinating gives no damages to seeds of broad leaf plants at all.

As mentioned above, a secure safety to the broadleaf crop against phytotoxicity of the herbicide is extremely high and as to its application, in the other weeds, its applicable time, its applying location and its applying concentration, it has a very broad extent and it can be used in the wider extent.

It is another advantage of the present invention that a residual toxicity in the soil or the plant and an acute toxicity for warm blooded animals and fishes are not feared because the said compounds can be employed with a low chemical concentration.

The compounds of this invention can be applied directly to the soil as pre-emergence treatment or as post-emergence treatment to plant foliage, or they can be mixed intimately with the soil, preferably post-emergence treatment to plant foliage, and may be applied to soil or plant foliar at rates of 50–1000g per 10 hectare, preferably 50–200g per 10 hectare, more preferably about 100g per 10 hectare.

The method of the present invention comprehends the employment of a liquid or solid composition containing one or more of the present compounds as an active ingredient.

The active ingredient of this invention may be formulated by mixing with suitable carriers in a form generally used in agricultural chemicals such as wettable powder, emulsifiable concentrate, dust formulation, granular formulation, water soluble powder and aerosol. As solid carriers, bentonite, diatomaceous earth, apatite, gypsum, talc, pyrophyllite, vercimulite, clay and others are used. As liquid carriers, kerosene, mineral oil, petroleum, solvent naphtha, benzene, xylene, cyclohexane, cyclohexanone, dimethylformamide, alcohol, acetone, and others are used. Sometimes surface active agent is added in order to give a homogeneous and stable formulation.

The compounds of this invention also can be applied admixed with other chemicals which are used in agronomic and horticultural management and are compatible with the compounds of this invention. Such chemicals can be, but are not restricted to, the classes of chemicals commonly known as plant nutrients, fertilizers, insecticides, acaricides, fungicides, herbicides and nematocides.

As for known herbicide it is recommended that the compound of the present invention is applied admixed with urea derivatives such as 3-(3,4-dichlorophenyl)-1-methoxy-1-methyl-urea, or N-(3,4-dichlorophenyl)N',-N'-dimethylurea, triazine derivatives such as 2-chloro-4-ethylamino-6-isopropylamino-s-triazine, or 2-chloro-4,6-bis(ethylamino)-s-triazine and amide derivatives such as N-1-naphthyl-phthalamic acid.

The concentrations of the active ingredients in the herbicidal composition of this invention vary according to type of formulation, and they are, for example, used in a range of 5 – 80 weight percent, preferably 10 – 60 weight percent, in wettable powder, 5 – 70 weight percent, preferably 20 – 60 weight percent, in emulsifiable concentrates, and 0.5 – 30 weight percent, preferably 1 – 10 weight percent in dust formulation.

Thus, a wettable powder or an emulsifiable concentrate produced thereto is diluted with water to a specified concentration and thereby, it is used as a liquid suspension or a liquid emulsion for treating soils or plant foliars. Further, a dust formulation is directly used for the soil treatment or the foliar treatment.

Examples of the Herbicidal Composition

Example 10

Wettable Powder

|  | Parts by weight |
|---|---|
| Compound 1 | 20 |
| Diatomaceous earth | 37 |
| Sodium alkylsulfate | 6 |
| Talc | 37 |

These are mixed homogeneously and reduced to fine particles. Consequently, wettable powder containing 20% of active ingredient is obtained. In practical use, it is diluted to a certain concentration with water and is sprayed as a suspension.

Example 11

Emulsifiable Concentrate

|  | Parts by weight |
|---|---|
| Compound 2 | 40 |
| Xylene | 35 |
| Dimethylformamide | 15 |
| Polyoxyethylene phenylether | 10 |

These are mixed and dissolved.

Consequently, emulsifiable concentrate containing 40% of the active ingredient is obtained. In practical use, it is diluted to certain concentration with water and then is sprayed as an emulsion.

Example 12

Dust Formulation

| | Parts by weight |
|---|---|
| Compound 3 | 7 |
| Talc | 38 |
| Bentonite | 10 |
| Clay | 38 |
| Sodium alkylsulfate | 7 |

These are mixed homogeneously and reduced to fine particles. Fine particles are made into granules having the diameter in the range of 0.5 – 1.0mm by a granulator.

Consequently, dust formulation containing 7% of the active ingredient is obtained. In practical use it is directly applied.

The superior herbicidal effect of the novel compounds of this invention is clearly illustrated by the following tests.

Test 1. Pre-emergence (soil treatment)

About 60 seeds of barnyard grass were planted in a pot having 60 square centimeters and covered slightly with soil. Said pot was kept in a state of stagnation so as to get wet with water.

10ml of an aqueous suspension prepared by diluting an emulsifiable concentrate with water to a specified concentration was sprayed on the pot. Two weeks after spraying, the degrees of damage to the plant were observed and estimated by the value of 0 – 5 which have the following meanings:

0: no effect
1: a few slightly burnt spots
2: marked damage to leaves
3: some leaves and parts of stalks partially dead
4: plant partially destroyed
5: plant completely destroyed or no germination The results were shown in Table 2.

Table 2

| Test compound No. | Application rate (g/10 are) | | | | |
|---|---|---|---|---|---|
| | 120 | 60 | 30 | 15 | 7.5 |
| 31 | — | — | 5 | 4 | 3 |
| 50 | — | — | 5 | 5 | 5 |
| 107 | — | — | 5 | 2 | 1 |
| 108 | — | — | 5 | 3 | 2 |
| 126 | — | — | 5 | 3 | 1 |
| 127 | — | — | 5 | 3 | 2 |
| 128 | — | — | 5 | 5 | 3 |
| 137 | — | — | 5 | 3 | 2 |
| 141 | — | — | 5 | 5 | 2 |
| 142 | — | — | 5 | 5 | 3 |
| 143 | — | — | 5 | 5 | 5 |
| 152 | — | — | 5 | 4 | 3 |
| 155 | — | — | 5 | 5 | 5 |
| Comparative compound | | 4 | 2 | 0 | 0 | 0 |
| Untreated | | | | | 0 |

Test 2. Post-emergence (foliar treatment)

About 50 seeds of barnyard grass were planted in a pot having 60 square centimeters and covered slightly with soil. Said pot was filled with water when the plant was grown to first leaf-stage.

An aqueous suspension prepared by diluting an emulsifiable concentrate with water to a specified concentration was sprayed on the pot. Two weeks after spraying, the degrees of damage to the test plant was observed and estimated by the value of 0 – 5 which have the same meanings as those of Test 1.

The results were shown in Table 3.

Table 3

| Test compound No. | Application rate (g/10 are) | | |
|---|---|---|---|
| | 125 | 62.5 | 31.3 |
| 10 | 5 | 4 | 3 |
| 18 | 5 | 5 | 4 |
| 31 | 5 | 5 | 4 |
| 50 | 5 | 5 | 4 |
| 107 | 5 | 5 | 4 |
| 108 | 5 | 5 | 3 |
| 112 | 5 | 4 | 1 |
| 124 | 5 | 3 | 1 |
| 126 | 5 | 4 | 3 |
| 127 | 5 | 4 | 3 |
| 128 | 5 | 4 | 4 |
| 135 | 5 | 3 | 1 |
| 137 | 5 | 5 | 4 |
| 141 | 5 | 5 | 4 |
| 142 | 5 | 5 | 5 |
| 143 | 5 | 5 | 5 |
| 150 | 5 | 4 | 3 |
| 152 | 5 | 5 | 5 |
| 154 | 5 | 4 | 3 |
| 155 | 5 | 5 | 4 |
| 156 | 5 | 5 | 4 |
| Comparative compound | | | |

Table 3-continued

| Test compound No. | Application rate (g/10 are) | | |
|---|---|---|---|
| | 125 | 62.5 | 31.3 |
| [structure: pyrone with OH, NOCH₂CH=CH₂, C-CH₃, CH₃] | 4 | 1 | 0 |
| [structure: Cl-C₆H₄-CH₂-S-C(O)-N(C₂H₅)₂] | 3 | 0 | 0 |
| Untreated | | 0 | |

Test 3. Pre-emergence

Seeds of large crab-grass was planted in a pot having 100 square centimeters. An aqueous suspension prepared by diluting an emulsifiable concentrate with water to a specified concentration was sprayed on the surface of the soil before emergence. 21 days after spraying, the degrees of damage to the test plant was observed and estimated by the value of 0 – 5 which have the same meanings as those of Test 1.

The results were shown in Table 4.

Test 4. Post-emergence (foliar treatment)

Seeds of large crab-grass was planted in a pot having 100 square centimeters. An aqueous suspension prepared by diluting an emulsifiable concentrate with water to a specified concentration was sprayed on the foliar of the test plant at a rate of 100 liter per 10 are.

21 days after spraying, the degrees of damage to the test plant was observed and estimated by the value of 0 – 5 which have the same meanings as those of Test 1. The results were shown in Table 5.

Table 4

| Test compound No. | Application rate (g/10 are) | | | | |
|---|---|---|---|---|---|
| | 300 | 120 | 60 | 30 | 15 |
| 31 | — | 5 | 5 | 5 | 4 |
| 50 | — | 5 | 5 | 5 | 5 |
| 75 | — | 5 | 5 | 5 | 5 |
| 83 | — | 5 | 5 | 5 | 5 |
| 96 | — | 5 | 5 | 5 | 4 |
| 107 | — | 5 | 4 | 2 | — |
| 111 | — | 5 | 4 | 1 | — |
| 126 | — | 5 | 3 | 1 | — |
| 127 | — | 5 | 4 | 2 | — |
| 128 | — | 5 | 4 | 2 | — |
| 134 | — | 5 | 3 | 1 | — |
| 137 | — | 5 | 2 | 0 | — |
| 142 | — | 5 | 5 | 4 | — |
| 143 | — | 5 | 4 | 4 | — |
| 152 | — | 5 | 5 | 5 | 4 |
| 154 | — | 5 | 5 | 4 | 3 |
| 155 | — | 5 | 5 | 4 | 4 |
| 156 | — | 5 | 5 | 4 | 4 |
| Comparative compound | | | | | |
| [structure: pyrone with OH, NOCH₂CH=CH₂, CH₃] | 4 | 0 | 0 | 0 | 0 |
| Untreated | | 0 | | | |

Table 5

| Test compound No. | Application rate (g/10 are) | | |
|---|---|---|---|
| | 100 | 50 | 25 |
| 10 | 5 | 5 | 5 |
| 18 | 5 | 5 | 5 |
| 31 | 5 | 5 | 4 |
| 50 | 5 | 5 | 5 |
| 75 | 5 | 5 | 4 |
| 83 | 5 | 5 | 5 |
| 106 | 5 | 3 | 2 |
| 108 | 5 | 5 | 4 |
| 125 | 5 | 4 | 4 |
| 126 | 5 | 5 | 4 |
| 127 | 5 | 5 | 4 |
| 128 | 5 | 5 | 4 |
| 134 | 5 | 4 | 3 |

Table 5-continued

| Test compound No. | Application rate (g/10 are) | | |
|---|---|---|---|
| | 100 | 50 | 25 |
| 135 | 5 | 4 | 3 |
| 137 | 5 | 4 | 2 |
| 141 | 5 | 5 | 4 |
| 142 | 5 | 5 | 4 |
| 143 | 5 | 5 | 5 |
| 145 | 5 | 3 | 2 |
| 152 | 5 | 5 | 5 |
| 154 | 5 | 4 | 4 |
| 155 | 5 | 5 | 5 |
| 156 | 5 | 5 | 4 |
| Comparative compound | | | |
| 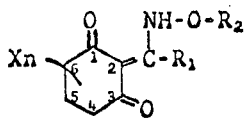 | 3 | 2 | 0 |
| 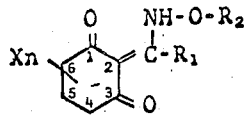 | 3 | 1 | 0 |
| Untreated | | 0 | |

What is claimed is:

1. A compound of the formula $$Xn \underset{5\ 4\ 3}{\overset{6\ 1\ 2}{\bigcirc}} \overset{O}{\underset{\parallel}{\overset{\parallel}{C}}} \overset{NH-O-R_2}{\underset{\parallel}{\overset{\parallel}{C-R_1}}} \\ O$$

wherein
$R_1$ is selected from the group consisting of hydrogen, alkyl and phenyl,
$R_2$ is selected from the group consisting of alkyl, straight or branched chain lower alkenyl, lower alkynyl, lower alkoxyalkyl, lower alkyl-thiomethyl and benzyl,
X is a same or different substituent which is selected from the group consisting of alkyl, halogen, phenyl, phenyl substituted with halogen or methoxy, styryl, 5,5-pentamethylene and 4,5-tetramethylene,
n is 0 or an integer from 1 to 6; or a hydrate or a light metal salt of the compound defined herein above.

2. A compound of the formula $$Xn \underset{5\ 4\ 3}{\overset{6\ 1\ 2}{\bigcirc}} \overset{O}{\underset{\parallel}{\overset{\parallel}{C}}} \overset{NH-O-R_2}{\underset{\parallel}{\overset{\parallel}{C-R_1}}} \\ O$$

wherein
$R_1$ is selected from the group consisting of hydrogen, alkyl of 1 to 5 carbon atoms and phenyl,
$R_2$ is selected from the group consisting of alkyl of 1 to 6 carbon atoms, straight or branched chain alkenyl of 3 to 4 carbon atoms, propargyl, alkoxymethyl of 1 to 4 carbon atoms, methoxyethyl, methylthiomethyl and benzyl,
X is a same or different substituent which is selected from the group consisting of alkyl of 1 to 6 carbon atoms, bromo, phenyl, chlorophenyl, methoxyphenyl, styryl, 5,5-pentamethylene and 4,5-tetramethylene,
n is 0 or an interger from 1 to 6; or a hydrate or a metal salt of the compound defined herein above, wherein the metal is selected from the group consisting of sodium, potassium, calcium, and barium.

3. A compound of the formula $$\underset{CH_3}{\overset{CH_3}{\bigcirc}} \overset{O}{\underset{\parallel}{\overset{\parallel}{C}}} \overset{NH-O-R_2}{\underset{\parallel}{\overset{\parallel}{C-R_1}}} \\ O$$

wherein
$R_1$ is selected from the group consisting of ethyl and propyl,
$R_2$ is selected from the group consisting of ethyl, propyl, allyl and propargyl.

4. A compound of the formula $$\underset{CH_3}{\overset{CH_3}{>}}CH \overset{O}{\underset{\parallel}{\overset{\parallel}{\bigcirc}}} \overset{NH-O-R_2}{\underset{\parallel}{\overset{\parallel}{C-R_1}}} \\ O$$

wherein
$R_1$ is selected from the group consisting of ethyl and propyl,
$R_2$ is selected from the group consisting of ethyl, propyl, allyl and propargyl.

5. A compound according to claim 3 in which $R_1$ is ethyl and $R_2$ is allyl.

6. A compound according to claim 3 in which $R_1$ is propyl and $R_2$ is allyl.

7. A compound according to claim 3 in which $R_1$ is propyl and $R_2$ is propargyl.

8. A compound according to claim 4 in which $R_1$ and $R_2$ are ethyl.

9. A compound according to claim 4 in which $R_1$ is ethyl and $R_2$ is allyl.

10. The sodium, barium and calcium salts of a compound of the formula

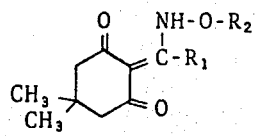

wherein
$R_1$ is selected from the group consisting of ethyl and propyl,
$R_2$ is selected from the group consisting of ethyl, propyl, allyl and propargyl.

11. The hydrate of a compound of the formula

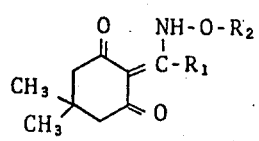

wherein
$R_1$ is selected from the group consisting of ethyl and propyl,
$R_2$ is selected from the group consisting of ethyl, propyl, allyl and propargyl.

* * * * *